(12) United States Patent
Li

(10) Patent No.: US 7,497,830 B2
(45) Date of Patent: Mar. 3, 2009

(54) THREE DIMENSIONAL ULTRASONIC IMAGING USING MECHANICAL PROBES WITH BEAM SCANNING REVERSAL

(75) Inventor: Xiang-Ning Li, Mill Creek, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 497 days.

(21) Appl. No.: 10/980,569

(22) Filed: Nov. 2, 2004

(65) Prior Publication Data

US 2005/0119576 A1    Jun. 2, 2005

Related U.S. Application Data

(60) Provisional application No. 60/524,303, filed on Nov. 21, 2003.

(51) Int. Cl.
*A61B 8/00* (2006.01)

(52) U.S. Cl. .................. 600/459; 600/437; 600/439; 600/443

(58) Field of Classification Search .............. 600/437, 600/443, 439, 459
See application file for complete search history.

(56) References Cited

U.S. PATENT DOCUMENTS

| | | |
|---|---|---|
| 4,468,747 A | 8/1984 | Leavitt |
| 4,581,636 A | 4/1986 | Blaker et al. |
| 5,460,179 A | 10/1995 | Okunuki et al. |
| 5,577,506 A * | 11/1996 | Dias ........................... 600/459 |
| 5,993,390 A | 11/1999 | Savord |
| 6,013,032 A * | 1/2000 | Savord ........................ 600/443 |
| 6,102,860 A | 8/2000 | Mooney |
| 6,126,602 A | 10/2000 | Savord |
| 6,375,617 B1 | 4/2002 | Fraser |
| 6,511,426 B1 * | 1/2003 | Hossack et al. ............. 600/437 |
| 6,905,465 B2 * | 6/2005 | Angelsen et al. ............ 600/437 |
| 2005/0090740 A1 * | 4/2005 | Raitzer et al. ............... 600/437 |
| 2005/0124887 A1 * | 6/2005 | Li ............................... 600/443 |

* cited by examiner

*Primary Examiner*—Long V Le
*Assistant Examiner*—Baisakhi Roy
(74) *Attorney, Agent, or Firm*—W. Brinton Yorks, Jr.

(57) ABSTRACT

An ultrasonic probe for three dimensional scanning includes a one-dimensional array transducer which is mechanically swept back and forth. As the array transducer is swept in one direction the array scans a volumetric region with image planes which are alternately scanned in opposite beam scanning directions to scan the volumetric region in a zigzag pattern. As the array transducer is swept in the opposite direction the volumetric region is again scanned with image planes of alternating beam scanning directions to again scan the volumetric region in a zigzag pattern. In a preferred embodiment the image planes scanned in one sweep direction intersect the centers of the image planes scanned in the other sweep direction, and the image planes of each sweep are approximately joined at their lateral edges.

16 Claims, 7 Drawing Sheets

THREE DIMENSIONAL ULTRASONIC IMAGING USING MECHANICAL PROBES WITH BEAM SCANNING REVERSAL

This invention claims the benefit of Provisional U.S. patent application Ser. No. 60/524,303, filed Nov. 21, 2003.

This invention relates to ultrasonic diagnostic imaging and, more particularly, to three dimensional ultrasonic imaging with a mechanically oscillating array.

Real time three dimensional ultrasonic diagnostic imaging systems have been constructed with both electronically steered and mechanically steered probes. Electronic beam steering is highly advantageous when scanning rapidly moving objects such as the heart. Real time three dimensional scanning probes with two dimensional arrays for cardiac scanning are described in U.S. Pat. No. 5,993,390 (Savord), U.S. Pat. No. 6,013,032 (Savord), U.S. Pat. No. 6,102,860 (Mooney), U.S. Pat. No. 6,126,602 (Savord), and U.S. Pat. No. 6,375,617 (Fraser), for example. Mechanical beam steering is advantageous for 3D abdominal scanning when a large aperture is desired. U.S. Pat. No. 5,460,179 (Okunuki et al.) shows a 3D imaging probe which mechanically sweeps a curved one-dimensional array within the probe. As the 1D array is swept, it scans image planes in the normal manner and those planes can then be processed to form a three dimensional image over the volume through which the image plane of the probe is swept.

However, mechanically sweeping an array probe as it is scanning presents problems due to the mechanical motion. When the probe is scanning as it is moving the scan planes will not be orthogonal to the direction of transducer motion but will be at a slight angle to that direction. This is because the probe is at a slightly different position along its path of travel with each transmitted and received beam. If the probe is scanned in both directions of travel the planes on the return sweep will be canted at a different angle than those of the forward sweep. This difficulty often manifests itself as a scintillating or shimmering effect in the image as the speckle pattern changes from one sweep to another. This problem can be eliminated by stepping the transducer array between discrete scanning positions, but the starting and stopping of the transducer array sweep will result in unacceptable sweep rates and hence less than acceptable real time imaging. Accordingly it is desirable to be able to sweep the transducer at a speed which provides real time 3D frame rates but without the creation of disturbing image artifacts.

In order to provide smooth real time three dimensional imaging it is desirable to mechanically scan the array transducer over the image volume at a relatively high scanning rate. However, a high scanning rate will mean that the volumetric region is scanned with fewer beams than would occur during a slower rate of scanning, which results in a decrease in spatial resolution in the 3D image. It would be desirable to be able to scan the transducer array at a high scan rate for smooth real time scanning, particularly in the presence of motion in the body, while still retaining the greater beam density and higher spatial resolution of a slower rate of scanning.

In accordance with the principles of the present invention, a three dimensional ultrasonic imaging probe includes an array transducer which is swept over a volumetric region being imaged. As the transducer is swept its beam scanning direction is periodically reversed. In one illustrated embodiment the beam scanning direction is reversed each time that the direction of travel of the array is reversed. In another embodiment the beam scanning direction is reversed with each successive scan plane.

In accordance with another aspect of the present invention the volumetric image is produced from the echo data acquired during multiple sweeps of the array transducer as it is scanned. Thus, the 3D image can exhibit greater spatial resolution due to the use of a greater number of received beams to produce the image. In accordance with a further aspect of the invention the scan conversion of echo data from multiple sweeps utilizes the relative temporal and spatial characteristics of the received echoes in the production of 3D image data.

Figure 5:
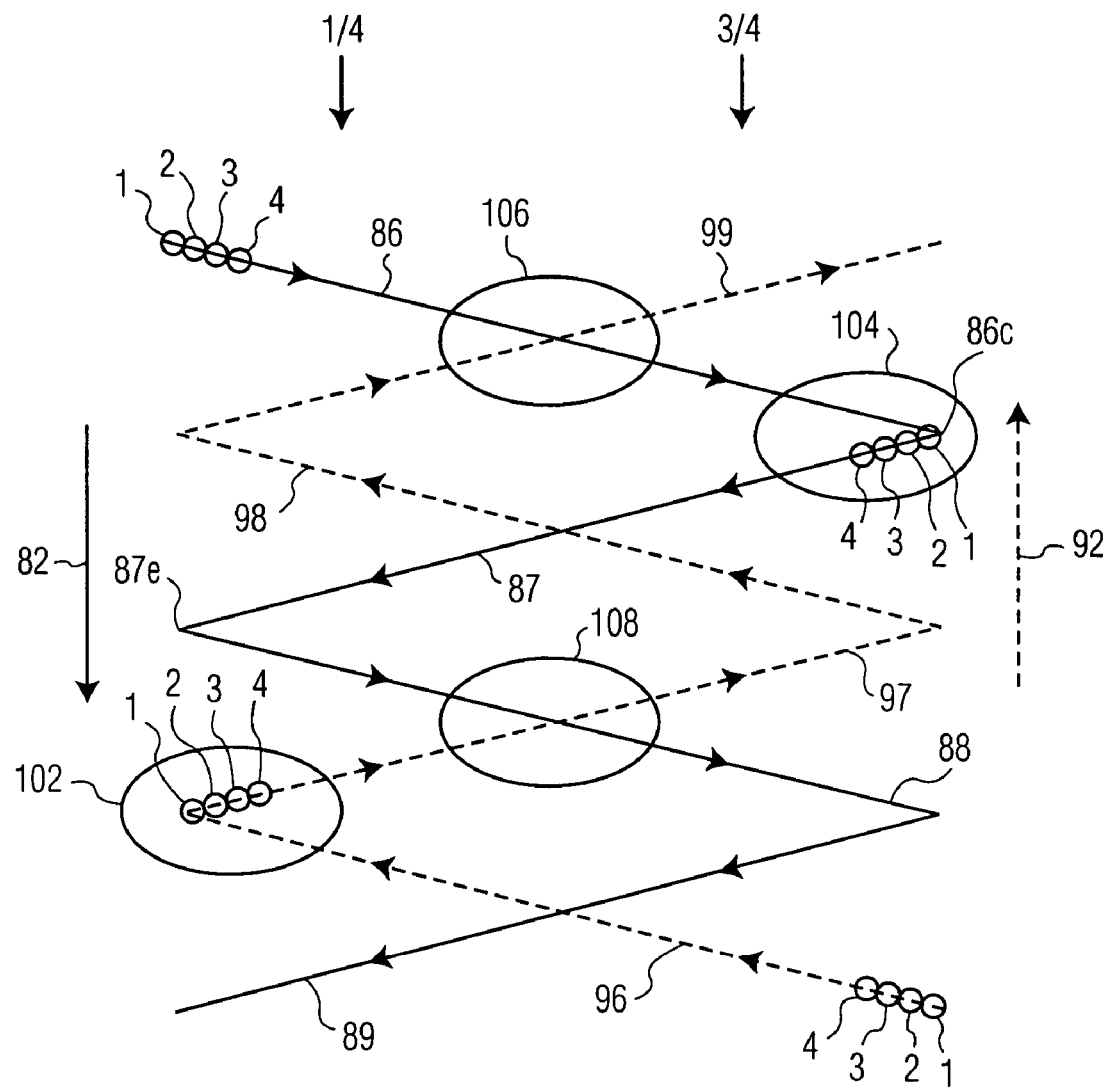
Figure 6:
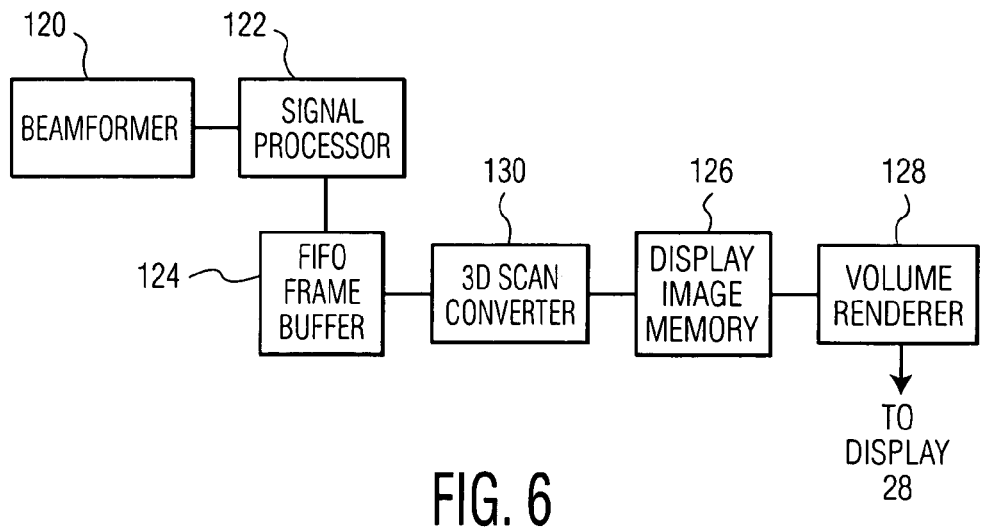
Figure 7:
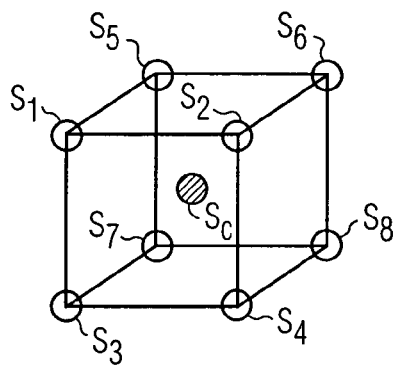
Figure 8:
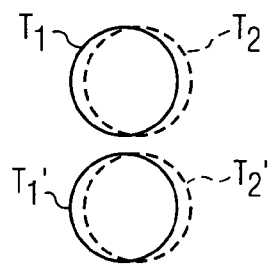

FIGS. 4$a$-4$d$ illustrate scan planes resulting from different beam scanning directions by a three dimensional imaging probe of the present invention;

FIG. 5 illustrates the scanning of a volumetric region with reversal of the beam scanning direction with successive scan planes;

FIG. 6 illustrates the receiver of a three dimensional imaging system with a scan converter for three dimensional imaging;

FIG. 7 illustrates the scan conversion of a three dimensional image value from surrounding acquired data values; and FIG. 8 illustrates the scan conversion of three dimensional echo data to form image display values, taking into consideration the spatial and temporal characteristics of the data.

Figure 1:
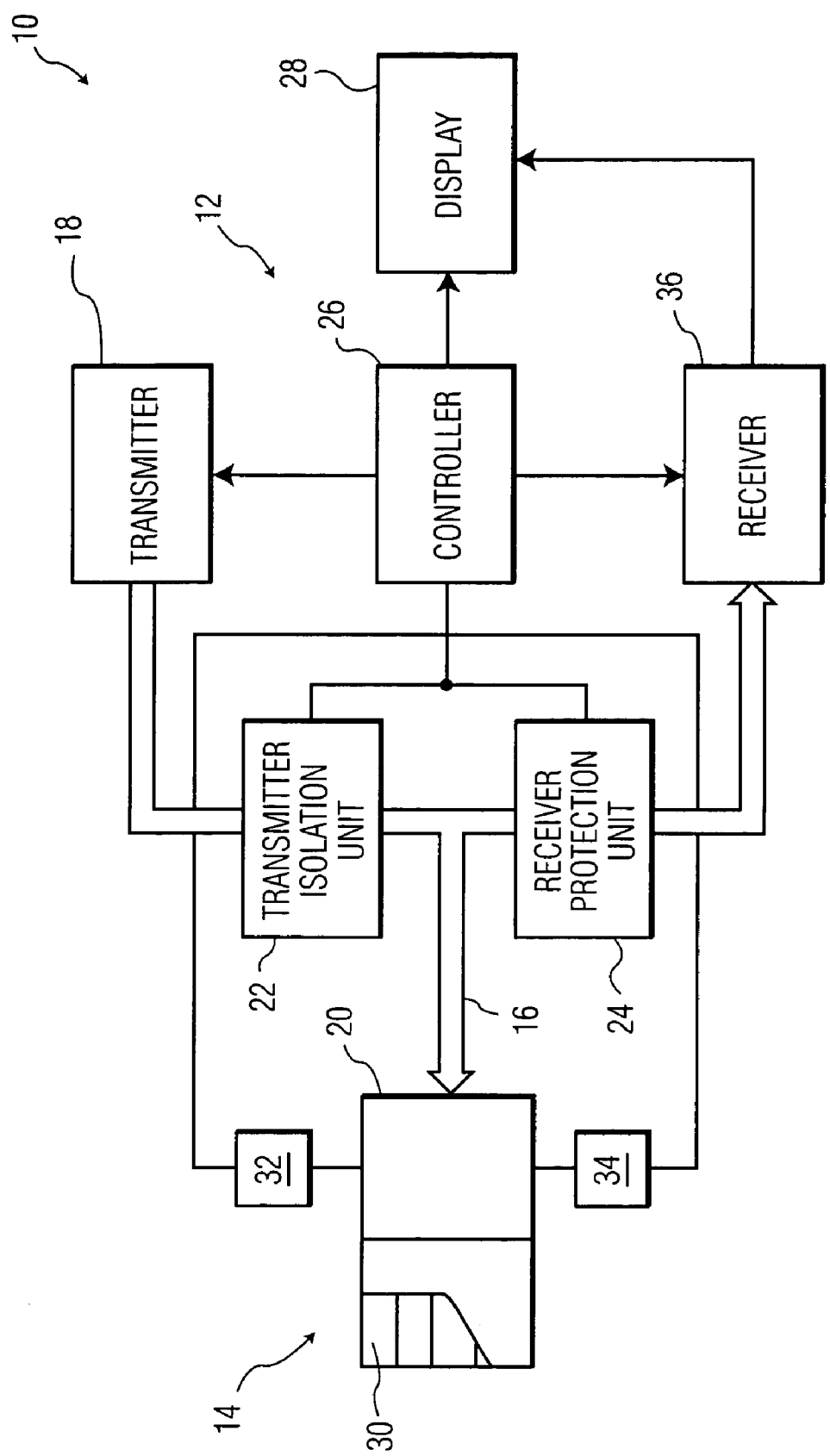
FIG. 1 illustrates in block diagram form an ultrasonic diagnostic imaging system constructed in accordance with the principles of the present invention.

Referring first to FIG. 1, an ultrasonic diagnostic imaging system 10 constructed in accordance with the principles of the present invention is shown in block diagram form. The system 10 includes an ultrasound processor 12 that is coupled to a probe or scan head 14 by a connecting cable 16. The ultrasonic processor 12 includes a transmitter 18 that generates signals at ultrasonic frequencies for emission by the scan head 14, and a receiver 36 to detect signals received by the scan head 14. In order to isolate the transmitter 18 from the scan head 14 while the receiver 36 is in operation, a transmitter isolation unit 22 decouples the transmitter 18 from the cable 16. Correspondingly, when the transmitter 18 is in operation, a receiver protection unit 24 decouples the receiver 36 from the cable 16. A controller 26 interacts with the transmitter 18, the receiver 36, the transmitter isolation unit 22 and the receiver protection unit 24 to coordinate the operation of these components. The controller 26 similarly interacts with a display system 28 to permit signals received by the processor 12 to be visually displayed.

The scan head 14 includes a transducer assembly 30 that is comprised of one or more piezoelectric elements that are configured to emit ultrasonic pulses in a desired direction when excited by signals generated by the transmitter 18, and to convert the reflected portions of the pulses into electrical signals that may be detected by the receiver 36. The transducer assembly 30 may include a one-dimensional array of transducer elements arranged in a planar, convex or even a concave arrangement of elements. In addition, the transducer assembly 30 may include other higher dimensional arrays of elements, such as a 1.5 or even a two-dimensional array.

Still referring to FIG. 1, the scan head 14 further includes a positional actuator 32 that is coupled to the transducer assembly 30 to position the transducer assembly 30 in a desired direction, and further to repetitively scan an anatomical region in the desired direction so that a real-time image of the region may be formed. The positional actuator 32 is coupled to the controller 26 through the cable 16 to transmit control inputs from the controller 26 to the actuator 32 so that the movement of the transducer assembly 30 may be controlled. The actuator 32 may be controlled, for example, by controlling a voltage or a current transferred to the actuator 32. Alternatively, the actuator 32 may be controlled by transferring a control signal from the controller 26 to a separate controller located within the scan head 14 that further controls a current or a voltage transferred to the actuator 32. The scan head 14 also includes a positional sensor 34 that is coupled to the transducer assembly 30. The positional sensor 34 determines the directional orientation of the transducer assembly 30 as it is moved by the positional actuator 32, and is similarly coupled to the controller 26 by the cable 16 to provide positional input signals to the controller 26.

Figure 2:
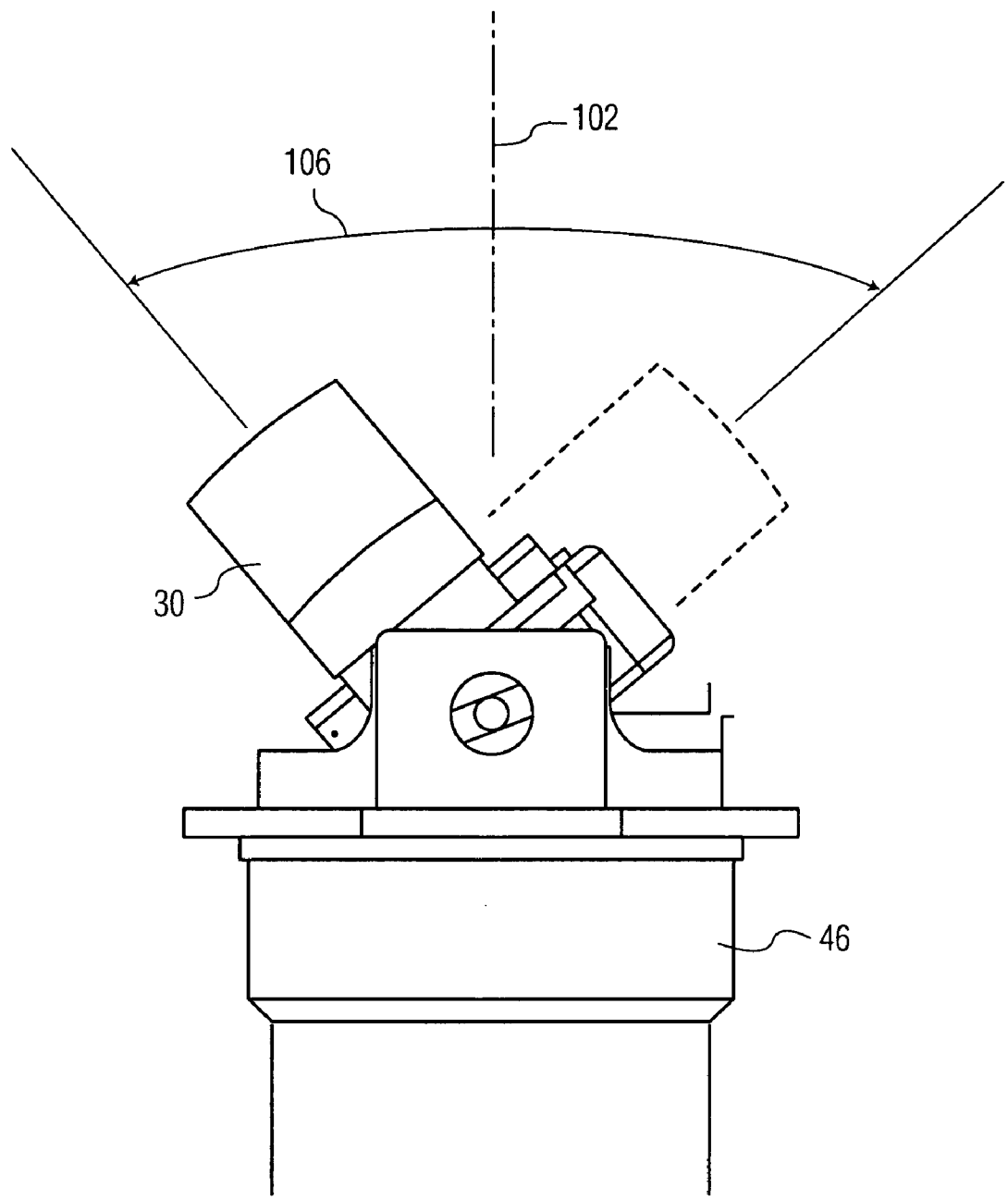
FIG. 2 illustrates the mechanical oscillation of an array transducer for three dimensional scanning.

Turning now to FIG. 2, a partial side view of a probe with a mechanically oscillating array transducer is shown. In FIG. 2, an axis 102 projects upwardly from FIG. 2, so that the transducer assembly 30 scans through a scanning angle 106. The scanning angle 106 may be centered about the axis 102, so that the transducer assembly 30 sweeps from the axis 102 to sweep angle limits that correspond to a complete rotation of a drive shaft 48 (discussed in conjunction with FIG. 3). Alternatively, the transducer assembly 30 may be swept through a scanning angle that is less than the scanning angle 106 by controlling a positional actuator 42 to rotate in a first direction less that a full revolution of the drive shaft 48, then rotating the drive shaft 48 in a second direction opposite to the first direction. Accordingly, scanning angles that are less than the scanning angle 106, which is the maximum obtainable scanning angle, may be conveniently obtained.

Still referring to FIG. 2, a positional actuator 42 (see FIG. 3) may also be controlled to sweep the transducer assembly 30 about an angle that is centered on another axis that is oriented at an angle with respect to the axis 102 so that the transducer assembly 30 may scan into anatomical regions that cannot be adequately scanned when the transducer assembly 30 is scanned through angles centered about the axis 102. For example, in performing an ultrasound scan in an upper abdominal or thoracic region, it is often difficult to properly position a scan head so that interfering reflections from ribs or other tissues are avoided. The ability to scan about an axis that is not aligned with a longitudinal axis of the support structure 46 of the scan head is therefore regarded as particularly advantageous.

Figure 3:
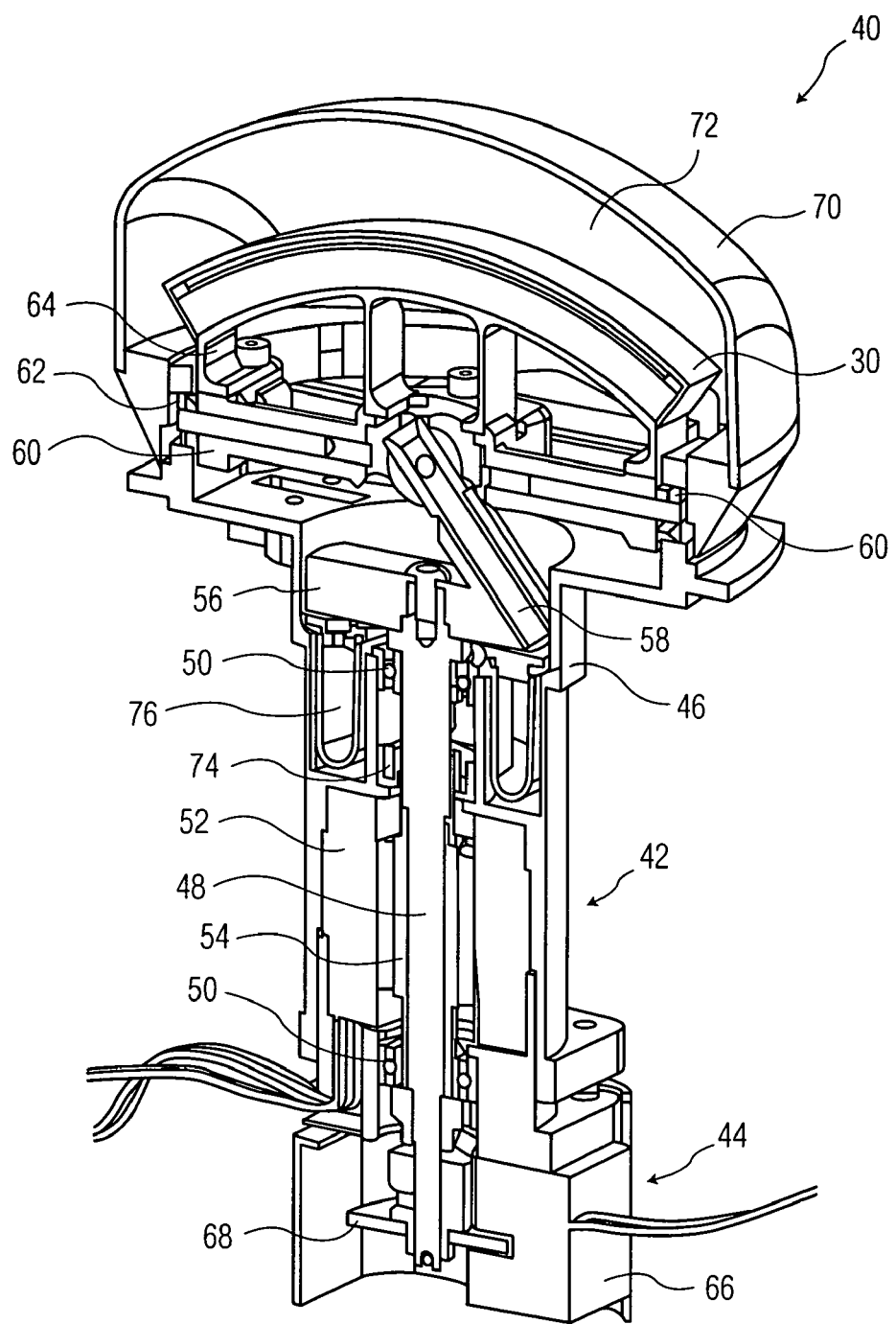
FIG. 3 illustrates a mechanism which mechanically oscillates an array transducer for three dimensional scanning.

FIG. 3 is a cross sectional isometric view of the 3D mechanical probe of FIG. 2 which is suitable for use in a constructed embodiment of the present invention. The probe 40 includes a positional actuator 42 that is mechanically coupled to the transducer assembly 30 and a positional sensor 44. The transducer assembly 30, the positional actuator 42 and the positional sensor 44 are positioned within a supporting structure 46. The positional actuator 42 includes a drive shaft 48 that extends upwardly from the positional sensor 44 along a longitudinal axis of the probe 40. The drive shaft 48 is rotatably supported within the supporting structure 46 of the probe 40 by bearings 50 positioned near respective ends of the drive shaft 48. The positional actuator 42 also includes an armature structure 52 that is stationary with respect to the supporting structure 46, and a permanent magnet field structure 54 coupled to the drive shaft 48. When the armature structure 52 is selectively energized, a torque is developed that rotates the drive shaft 48 in a desired rotational direction so that the drive shaft 48 and the field structure 54 form a driven member. The armature structure 52 may also be selectively energized to rotate the drive shaft 48 in increments of less than a full rotation, and/or at different rotational rates during the rotation of the drive shaft 48.

The positional actuator 42 further includes a crank member 56 that is coupled to the drive shaft 48, which rotatably couples to a lower, cylindrical-shaped portion of a connecting member 58. The relative position of the crank member 56 with respect to the supporting structure 46 allows adjustment of the mechanical sweeping range of the transducer array assembly 30. An upper end of the connecting member 58 is hingeably coupled to a pivot member 60 that is axially supported on the structure 46 by a pair of bearings 62. The pivot member 60 further supports a cradle 64 that retains the transducer assembly 30. Although not shown in FIG. 3, the cradle 64 may also include electrical contacts so that individual elements in the transducer assembly 30 may transmit and receive ultrasonic signals, as more fully described above. The contacts may further be coupled to a conductive assembly, such as a flex circuit, that is coupled to the processor 12, as shown in FIG. 1. Briefly, and in general terms, rotational motion imparted to the crank member 56 by the drive shaft 48 produces an oscillatory motion in the pivot member 60, which permits the transducer assembly 30 to be moved through a selected scan angle.

The positional sensor 44 includes a counter 66 that is stationary with respect to the supporting structure 46, and an encoding disk 68 that is fixedly coupled to the drive shaft 48, so that the encoding disk 68 and the drive shaft 48 rotate in unison. The encoding disk 68 includes a plurality of radially-positioned targets that the counter 66 may detect as the encoding disk 68 rotates through a gap in the counter 66, thus generating a positional signal for the shaft 48. Since the angular position of the array 30 may be correlated with the rotational position of the shaft 48, the encoding disk 68 and the counter 66 therefore cooperatively form a sensor capable of indicating the angular orientation of the array 30. In one particular embodiment, the encoding disk 68 and the counter 66 are configured to detect the rotational position of the drive shaft 48 by optical means. The disk 68 and the counter 66 may also be configured to detect the rotational position of the drive shaft 48 by magnetic means, although still other means for detecting the rotational position of the drive shaft 48 may also be used. In still another particular embodiment, the encoding disk 68 and the counter 66 are configured to have an angular resolution of at least 1000 counts per revolution.

Still referring to FIG. 3, the probe 40 further includes a cover 70 that is coupled to the supporting structure 46. The cover 70 is formed from a material that is acoustically transparent at ultrasonic frequencies. The cover 70 further partially defines an internal volume 72 that sealably retains an acoustic coupling fluid (not shown) that permits ultrasonic signals to be exchanged between the transducer assembly 30 and the cover 70 by providing a suitable acoustic impedance match. In one aspect, a silicone-based fluid may be used that also provides lubrication to the mechanical elements positioned within the volume 72. A shaft seal 74 is positioned within the supporting structure 46 that surrounds the drive shaft 48 to substantially retain the acoustic coupling fluid within the volume 72. The internal volume 72 further includes an expandable bladder 76 that is positioned below the crank member 56 to permit the fluid retained within the volume 72 to expand as the fluid is heated or exposed to low pressure, thus preventing leakage of the fluid from the volume 72 that may result from excessive fluid pressures developed within the probe 40.

Figure 4A:
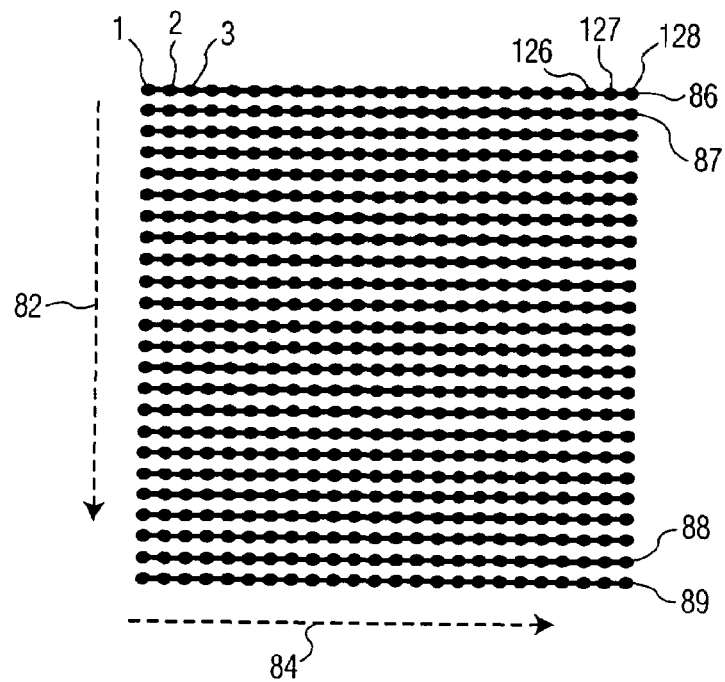

In use, a mechanical scanning array probe such as that of FIGS. 2 and 3 will transmit and receive beams as the array is moved back and forth in opposition to the region of the body being scanned. It is well known that the speckle pattern generated by adjacent coherent beams is established by the relationship of the transmit and receive apertures to the scatterer field of the underlying tissue. If the aperture/scatterer relationship is changing, a scintillating or shimmering effect is produced in the image as the speckle pattern continually changes its appearance. One way to stabilize the speckle pattern against such artifacts is to ensure that the transmit/receive aperture is continually in the same spatial location during scanning. FIG. 4a illustrates a scanning pattern which accomplishes this stabilization. In this drawing each horizontal line represents the beams of a scan plane as viewed axially, that is, from the perspective of the array transducer. In this embodiment the array is stepped from one scanning position to another. The illustrated sequence begins by transmitting a first scan plane 86, followed by a second scan plane 87 and so forth, and ending with scan planes 88 and 89. The arrow 82 indicates the direction of travel of the array transducer from one scan plane location to another. After scan plane 89 has been transmitted and received the array transducer either returns to its starting position (scan plane 86), or reverses its sweep direction and scans scan plane 88 and then back to scan plane 86. When the array is halted at each new scanning position an image plane is scanned by a series of beams 1, 2, 3, . . . 126,127,128 which are transmitted from left to right as indicated by the arrow 84. However, the time required to start and stop the array transducer at each scan plane location is considerable. Thus, the time needed to acquire echo signals from the complete volume being scanned is excessive and the volume frame rate will be extremely low.

Figure 4B:
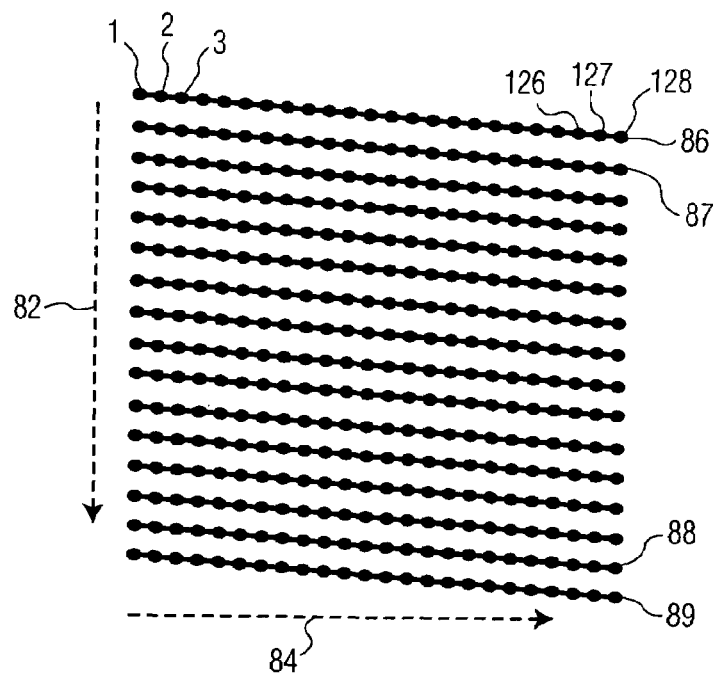
Figure 4C:
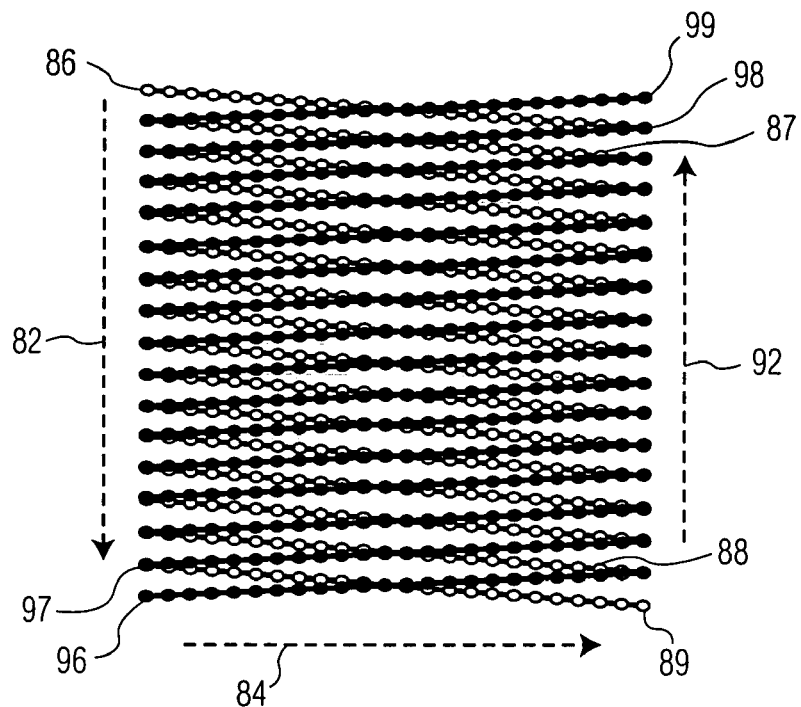

To improve the volume frame rate to at or near real time, it is necessary to transmit and receive beams for the scan planes as the array transducer is continually moving. The array only stops momentarily at the end of a sweep when its scanning direction is changed. This results in a parallelogram-shaped scanning pattern as shown in FIG. 4b, rather than the rectangular pattern of FIG. 4a. This is due to the fact that the array transducer is ever so slightly advanced in its direction of travel 82 as each successive beam 1,2,3, . . . 126,127,128 is transmitted and received. However this scanning sequence gives rise to a problem when the sweep direction 82 of the array transducer is reversed, as shown in FIG. 4c. In this drawing the sequence of grey-shaded scan planes 86,87 . . . 88,89 are those acquired when the transducer array is moved in the direction 82. The blackened scan plane sequence 96,97, . . . 98,99 are those acquired when the sweep direction of the transducer array is reversed, as indicated by the direction of travel arrow 92. As this drawing illustrates, the scan planes are tilted at an inverse angle when the scanning direction of the array transducer is reversed. This causes the scan planes of the respective scanning directions to intersect but never to overlap. Hence the apertures on the forward and reverse scanning directions will be different, giving rise to the shimmering artifact.

Figure 4D:
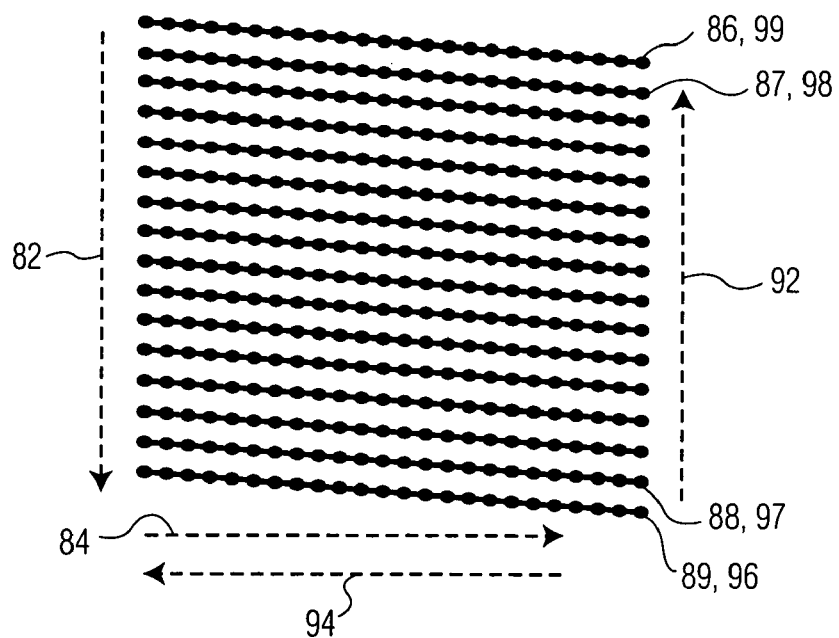

In accordance with a first aspect of the present invention, the order of beam firing is reversed with the array sweep direction is reversed, as shown in FIG. 4d. When the array transducer is moving in the forward direction 82 the transducer beams are fired from left to right as shown by arrow 84. When the array transducer is moving back in the reverse direction 92, the beams are fired from right to left as indicated by arrow 94. As a consequence, the transducer array on its return sweep will overlie the same points and fire any given beam into the same tissue region as it did on the forward sweep. This ensures that the scatterer field seen by the beam pattern in the forward sweep direction is identical to that of the reverse sweep direction. This causes the speckle pattern from sweep to sweep to be stable without the blurring effect of methods that combine data from sequential volumes.

When the movement of the aperture is very fast relative to the beams firing time, the beams can be axially "bent" in appearance, a problem which can be corrected by "hose" correction.

In accordance with another aspect of the present invention, the beam firing direction is reversed, not with each array sweep direction change, but with each scan plane. The beams of successive scan planes will thereby take on a zigzag appearance as shown in FIG. 5. In this example a first scan plane 86 is scanned from left to right as indicated by the small circles 1,2,3,4, which represent successive beams which are transmitted and received from the left side of the array transducer to the right, as indicated by the arrowheads drawn on the scan plane 86. As the last beam of scan plane 86 is transmitted and received at the end 86c of the scan plane, the direction of beam transmission is reversed for the next scan plane 87. This scan plane 87 is then scanned from right to left starting with the beams shown as small circles 1,2,3,4. This scan plane 87 is scanned until the plane has been fully scanned with the last beam transmitted and received at the end 87e of the scan plane 87. The direction of beam scanning by the array transducer is again reversed and the next scan plane 88 is scanned from left to right, and the succeeding scan plane 89 is scanned from right to left, both as indicated by the arrowheads drawn on the scan planes.

When the array transducer has reached the end of its sweep in the direction 82, it reverses its sweep direction as indicated by the dashed arrow 92. A series of scan planes 96 . . . 99, shown in dashed lines, is then scanned as the array transducer sweeps back to its initial position. It is seen that the volume scanned by the scan planes is thereby scanned with a series of angled scan planes covering the volume in a zigzag pattern of scan planes. For some applications this scanning pattern may provide more complete spatial scanning and hence better images than the series of parallel, fully overlapping scan planes of FIG. 4d.

In accordance with another aspect of the present invention, more detailed 3D images are produced by using the data acquired during two successive sweeps of the array transducer to form the images. In the example of FIG. 5, this would mean that the echo data of planes 86 . . . 89 of the first (direction 82) sweep of the array and the echo data of planes 96 . . . 99 of the second (direction 92) sweep of the array are used to form one image. When the array transducer completes a third sweep in the direction 82, the data from this third sweep and the data from the second sweep of the array are used to form the next 3D image in the sequence. The older data of the first sweep in direction 82 is replaced by the new data of the subsequent sweep in direction 82 to form the new 3D image. The third 3D image in the sequence would be formed by the data of the third sweep in direction 82 and the data of a fourth sweep in direction 92. In this way, detailed 3D images are formed with a relatively high frame rate of display.

The details of a receiver 36 (FIG. 1) for receiving and processing this scan data is shown in FIG. 6. A beamformer 120 receives echo signals from the elements of the transducer assembly 30 and forms coherent receive beams. The coherent echo data is coupled to a signal processor 122 which processes the echo data as by filtering, harmonic separation, B mode detection or Doppler detection in accordance with the imaging mode being used. The received beams are then stored in a FIFO frame buffer 124.

When all of the scan planes needed to form a 3D image have been stored in the FIFO frame buffer 124 the echo data is coupled to a 3D scan converter 130, the operation of which will be discussed more fully below. The scan converted data is stored in a display image memory 126, which may typically store the data in an x,y,z three dimensional format. The data needed to produce a display frame is coupled to a volume renderer 128 which renders a three dimensional image by any of a variety of known rendering techniques. The volume rendered image is then coupled to the display 28 for display of the three dimensional image.

Returning to FIG. 5, it can be seen that the data acquired by scan planes 86-99 exhibits a number of characteristics. For instance, at the ¼ and ¾ positions in the lateral (left-right) dimension, the scan planes are relatively uniformly separated (below the ¼ and ¾ arrows), providing relatively uniform spatial sampling of the volume being imaged. However, at the lateral edges and in the center, the spatial sampling is less uniform in the elevation (sweep) direction. In addition, the data at these lateral-most and central locations exhibit different temporal characteristics, examples of which are circled by ovals 102 and 104. All of the echo data from beams within oval 102 are acquired at the end of scan plane 96 and at the beginning of scan plane 97 of the reverse sweep when the array transducer is moving in direction 92. Thus, motion artifacts would not be a serious problem in this region of the volumetric display.

However in the center of the image there are different temporal characteristics. In oval 108 the scan plane data is in close spatial identity as the image planes intersect in this region. But the image plane data is from image planes which are relatively greatly separated in time, as the data of scan plane 88 was acquired during the first (direction 82) sweep, whereas the data of scan plane 97 was acquired during the second (direction 92) sweep. The scan plane data of oval 106 is even more temporally disparate, as the data of scan plane 86 was acquired at the beginning of the first sweep in direction 82, whereas the data of scan plane 99 was acquired at the end of the second sweep in direction 92. The possibilities of motion artifact are therefore the greatest in this region. To guard against these motion artifacts, more temporal interpolation will be used when combining data in this region. However, when the third sweep begins and the data within the oval 106 consists of the data from scan plane 99 at the end of the second sweep and the data from the first scan plane (86') of the third sweep, the great temporal disparity is no longer present. When this scan plane data is combined, little temporal interpolation is needed as motion artifacts will be relatively low.

To take these disparities into consideration, in accordance with a further aspect of the present invention, 3D scan conversion is performed by spatial and temporal weighting of data values being combined which varies with the different spatial and temporal characteristics of the data which is being combined.

This may be appreciated by considering the type of signal combination which is performed in scan conversion. One common type of scan conversion is four-point interpolation as described in U.S. Pat. No. 4,468,747 (Leavitt)(see FIG. 7A) and U.S. Pat. No. 4,581,636 (Blaker et al.)(see FIG. 2), which show this technique as applied to scan conversion for two dimensional images. In general, four-point interpolation locates the four acquired data values at corners of a quadrilateral area in which the image point to be determined is located. The image point is produced by combining the four data values with weights which are a function of their spatial distance from the image point being determined. This technique may be applied to three dimensional scan conversion as shown by FIG. 7. In this example a center image point $S_c$ is to be determined. The value of image value $S_c$ is found by considering the eight acquired data values $S_1$-$S_8$ at the corners of a volume enclosing the image point $S_c$. The value of $S_c$ would be determined by combining the values of data points $S_1$-$S_8$ as a function of the distance from image point $S_c$. In practice the number of data points being combined can vary. It can be as large as a cluster of data values in the vicinity of the image point being calculated. Data point clusters of sixteen, thirty-two and sixty-four values have been used in constructed embodiments of the present invention, and greater or lesser numbers of values may also be used.

A simple example of spatial and temporal weighting which may be used in an embodiment of the present invention is illustrated in FIG. 8, in which four acquired data values are combined to form an image value. In this example data values $T_1$ and $T_2$ are virtually identical spatially, as are data values $T_1'$ and $T_2'$. This is indicated in the drawing by the almost complete overlap of the circles of $T_1$ and $T_2$ on one hand, and the circles of $T_1'$ and $T_2'$, on the other. The data values $T_1$ and $T_1'$ are nearly identical temporally, with both being acquired during the same sweep of the array transducer. Likewise, in this example the data values $T_2$ and $T_2'$ are nearly identical temporally. The data values $T_1$ and $T_2$, which are substantially identical spatially, are spatially offset from the similarly spatially identical data values $T_1'$ and $T_2'$. These conditions could arise, for instance, when data values are acquired at the intersection of scan planes 86 and 99, where the acquired data values of the two scan planes could be spatially identical yet temporally separate, as each was acquired during a different sweep of the array transducer.

If these four data values were being combined to determine a scan converted image value in the region of oval 106, temporal interpolation may be emphasized to reduce potential motion artifacts, due to the large temporal difference between scan planes 86 and 99. For example, the temporal weighting may be emphasized by a temporal weight of 60% as compared with a 40% spatial weighting. A scan converted value between these data points would thus be of the form:

$$T_I = 0.6\left(\frac{T_2 + T_2'}{2}\right) + 0.4\left(\frac{T_1 + T_1'}{2}\right)$$

If these data values were from the region of oval 108 where less temporal interpolation would be needed, as scan planes 88 and 97 are more closely acquired in time and present a lesser possibility of spatial artifacts, then spatial weighting could be emphasized more greatly than temporal weighting. Again exemplary weights of 60% and 40% are used, and the scan conversion formula would be of the form:

$$T_I = 0.6\left(\frac{T_1 + T_2}{2}\right) + 0.4\left(\frac{T_1' + T_2'}{2}\right)$$

By varying the weighting of scan conversion to take into consideration the spatial and temporal aspects of the data being combined, the high spatial line density resulting from combining frames of two or more sweeps can be provided with temporal resolution which is relatively low in artifacts.

It will be appreciated that the same zigzag coverage of the volume being scanned can be accomplished by reversing the beam scanning direction from frame to frame, as shown in FIG. 5, or by maintaining the same beam scanning direction through both sweeps as shown in FIG. 4c. In either case, the selective spatial and temporal weighting described above can be employed to produce high quality images that are low in temporal artifacts.

What is claimed is:

1. An ultrasonic diagnostic imaging system which acquires three dimensional image data sets by the scanning of a one-dimensional array transducer comprising:
   an array transducer including an array of transducer elements extending in an azimuth dimension and an elevation dimension normal to the azimuth dimension;
   a motive device, coupled to the array transducer, which acts to sweep the array transducer in reciprocating directions substantially in the elevation dimension; and
   a transmitter, coupled to the array transducer, which acts to cause the array transducer to transmit a plurality of sequences of beams in the azimuth direction while the array transducer is swept in each of the reciprocating directions, wherein successive sequences of beams are transmitted in opposite directions in the azimuth dimension during each reciprocating sweep.

2. The ultrasonic diagnostic imaging system of claim 1, wherein the array transducer comprises a one-dimensional array transducer; and
   wherein the motive device comprises an oscillating mechanism which acts to sweep the array transducer in a forward direction from a first turn-around position to a second turn-around position, and in a reverse direction from the second turn-around position to the first turn-around position.

3. The ultrasonic diagnostic imaging system of claim 2, wherein the transmitter further comprises a transmitter which acts to cause the array transducer to transmit a plurality of sequences of beams which scan a three dimensional image field in a zigzag pattern as the array transducer is swept in the forward direction and as the array transducer is swept in the reverse direction.

4. The ultrasonic diagnostic imaging system of claim 3, wherein the transmitter further comprises a transmitter which acts to cause the array transducer to scan a first series of scan planes as the array transducer is swept in the forward direction, and acts to cause the array transducer to scan a second series of scan planes which intersect the scan planes of the first series as the array transducer is swept in the reverse direction.

5. The ultrasonic diagnostic imaging system of claim 2, wherein the transmitter further comprises a transmitter which acts to cause the array transducer to repetitively transmit sequences of beams from the left side of the array transducer to the right side of the array transducer and from the right side of the array transducer to the left side of the array transducer when the motive device is sweeping the array transducer in the forward direction, and acts to cause the array transducer to repetitively transmit sequences of beams from the right side of the array transducer to the left side of the array transducer and from the left side of the array transducer to the right side of the array transducer when the motive device is sweeping the array transducer in the reverse direction.

6. The ultrasonic diagnostic imaging system of claim 5, wherein the transmitter further comprises a transmitter which acts to cause the array transducer to scan a series of scan planes as the array transducer is swept in the forward direction, and acts to cause the array transducer to scan an intersecting series of scan planes as the array transducer is swept in the reverse direction.

7. A method for scanning a volumetric object with a moving array transducer having a plurality of elements extending in an azimuth dimension and exhibiting an elevation dimension normal to the azimuth dimension comprising:
   sweeping the array transducer in a forward direction which is substantially in the elevation dimension of the array transducer;
   actuating the elements of the array transducer to transmit a first sequence of beams in a first azimuth direction and a second sequence of beams in a second azimuth direction as the array transducer is swept in the forward direction;
   sweeping the array transducer in a reverse direction which is substantially in the elevation dimension of the array transducer; and
   actuating the elements of the array transducer to transmit a third sequence of beams in the second azimuth direction and a fourth sequence of beams in the first azimuth direction as the array transducer is swept in the reverse direction.

8. The method of claim 7, wherein sweeping the array transducer in the forward direction comprises sweeping the array transducer from a first turn-around position to a second turn-around position; and
   wherein sweeping the array transducer in the reverse direction comprises sweeping the array transducer from the second turn-around position to the first turn-around position.

9. The method of claim 8, wherein actuating the elements of the array transducer to transmit first and second sequences of beams further comprises transmitting a sequence of beams from left to right in the azimuth direction and transmitting a sequence of beams from right to left in the azimuth direction; and
   wherein actuating the elements of the array transducer to transmit third and fourth sequences of beams further comprises transmitting a sequence of beams from right to left in the azimuth direction and transmitting a sequence of beams from left to fight in the azimuth direction.

10. The method of claim 8, wherein actuating the elements of the array transducer to transmit first and second sequences of beams further comprises transmitting a sequence of beams of a scan plane from left to right in the azimuth direction and transmitting a sequence of beams of a scan plane from right to left in the azimuth direction; and
    wherein actuating the elements of the array transducer to transmit third and fourth sequences of beams further comprises transmitting a sequence of beams in an intersecting scan plane from fight to left in the azimuth direction and transmitting a sequence of beams in an intersecting scan plane from left to right in the azimuth direction.

11. A method for scanning a volumetric object with a moving array transducer having a plurality of elements extending in an azimuth dimension and exhibiting an elevation dimension normal to the azimuth dimension comprising:
    sweeping the array transducer in a forward direction which is substantially in the elevation dimension of the array transducer;
    scanning a first sequence of scan planes which traverse an image region of the volumetric object in a zigzag pattern as the array transducer is swept in the forward direction;
    sweeping the array transducer in a reverse direction which is substantially in the elevation dimension of the array transducer; and scanning a second sequence of scan planes which traverse the image region in a zigzag pattern as the array transducer is swept in the reverse direction.

12. The method of claim 11, wherein scanning a sequence of scan planes comprises scanning a sequence of alternating angled scan planes which traverse the image region of the volumetric object.

13. The method of claim 11, wherein the sequence of scan planes which is scanned as the array transducer is swept in the forward direction intersects the sequence of scan planes which is scanned as the array transducer is swept in the reverse direction.

14. The method of claim 13, wherein the scan planes of the first sequence intersect the scan planes of the second sequence at approximately the center of the image region.

15. The method of claim 14, wherein the lateral edge of at least one of the scan planes of each sequence approximately intersects the lateral edge of another one of the scan planes of the sequence.

16. The method of claim 11, wherein successive scan planes in each sweep direction are scanned in opposite beam scanning directions.

* * * * *